(12) United States Patent
Bohlmann et al.

(10) Patent No.: US 7,080,561 B2
(45) Date of Patent: Jul. 25, 2006

(54) VISUAL DOCUMENTATION OF MICRO-CRACKS DURING TENSILE COUPON TESTING

(75) Inventors: Raymond E. Bohlmann, St. Louis, MO (US); Milton D. Hurd, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 94 days.

(21) Appl. No.: 10/950,755

(22) Filed: Sep. 27, 2004

(65) Prior Publication Data

US 2006/0070452 A1    Apr. 6, 2006

(51) Int. Cl.
*G01L 1/24*    (2006.01)
(52) U.S. Cl. .................................................. 73/800
(58) Field of Classification Search ................. 73/799, 73/800
See application file for complete search history.

(56) References Cited

U.S. PATENT DOCUMENTS

| | | | | |
|---|---|---|---|---|
| 4,836,029 A * | 6/1989 | Skala et al. | ................ | 73/799 |
| 5,165,287 A * | 11/1992 | Manahan, Sr. | ................ | 73/851 |
| 5,539,656 A * | 7/1996 | Annigeri et al. | ................ | 702/35 |
| 5,668,324 A * | 9/1997 | Voss et al. | ................ | 73/800 |
| 5,673,203 A * | 9/1997 | Annigeri et al. | ................ | 702/42 |
| 5,799,103 A * | 8/1998 | Schneider et al. | ................ | 382/141 |
| 5,883,311 A * | 3/1999 | Hettiarachchi et al. | ................ | 73/799 |
| 6,006,608 A * | 12/1999 | Renz et al. | ................ | 73/800 |
| 6,094,259 A * | 7/2000 | Kamegawa | ................ | 356/32 |
| 6,359,446 B1 | 3/2002 | Little, Jr. | | |
| 6,460,418 B1 * | 10/2002 | Hiyoshi | ................ | 73/800 |
| 2003/0066356 A1 * | 4/2003 | Kanellopoulos et al. | ...... | 73/800 |
| 2003/0215196 A1 * | 11/2003 | Bulters et al | ................ | 385/100 |
| 2004/0225346 A1 * | 11/2004 | Mazumder et al. | ........ | 623/1.13 |
| 2005/0082343 A1 * | 4/2005 | Wang et al. | ................ | 228/115 |
| 2005/0131662 A1 * | 6/2005 | Ascenzi et al | ................ | 703/11 |

OTHER PUBLICATIONS

Scott T. Burr, David L. Sikarskie, "Damage Characterization of Woven Composites Under Static Tensile Loading", Proceeding of the 1995 SEM Spring Conference and Exhibit, Jun. 12-14, 1995, Grand Rapids, MI, USA.

* cited by examiner

*Primary Examiner*—Edward Lefkowitz
*Assistant Examiner*—George P Bonanto
(74) *Attorney, Agent, or Firm*—Shimokaji & Associates, P.C.

(57) ABSTRACT

A test method for visual documentation of micro-cracks during tensile coupon testing includes the steps of: assembling a test unit; inserting a carbon-reinforced composite specimen having a prepared edge into the tensile coupon testing machine; illuminating the prepared edge of the specimen with a camera strobe light and a microscope light; applying a tensile load to the specimen; and capturing images (at 10% increments of the expected failing stress) of the prepared edge of the specimen with a digital camera that is attached to a stereomicroscope. Using the test method of the present invention photographic documentation of the formation and growth of micro-cracks in carbon-reinforced composite materials under tensile load is possible. The obtained data may be used to avoid or limit fatigue failure of carbon-reinforced structures used, for example, in the aerospace industry, for example, in spacecrafts and advanced military aircraft.

33 Claims, 8 Drawing Sheets

VISUAL DOCUMENTATION OF MICRO-CRACKS DURING TENSILE COUPON TESTING

BACKGROUND OF THE INVENTION

The present invention generally relates to composite materials and tensile coupon testing and, more particularly, to carbon-reinforced composite materials and a test method for visual documentation of the formation and growth of micro-cracks in these materials during tensile coupon testing.

The requirements for material used in the aerospace industry are manifold. Demands include improved toughness, lower weight, as well as increased resistance to fatigue and corrosion. The boundaries of material properties are being constantly extended as manufacturers strive to give the next generation of aircraft improved performance while making them more efficient. The use of fiber-reinforced composite materials over metals and their alloys over the past 20 years has increased significantly because of the weight savings and the improvement in fatigue life and corrosion control. Fiber-reinforced composite materials contain a strong and stiff fiber, such as a carbon fiber, embedded in a softer matrix material, such as a resin. Laminated composite materials generally exhibit an initial stiffness that is used in the design of structures. Laminated composites are constructed of many layers of fiber-reinforced materials. Fiber-reinforced polymer matrix composites, such as carbon (graphite)/epoxy and carbon/cyanate ester are now the materials of choice for spacecraft and launch vehicle structures and subsystems such as optical benches, instruments, and antennas. Furthermore, fiber-reinforced polymer matrix composites are widely used in commercial and military aircraft, sports equipment, and industrial and medical equipment. For example, composite structure utilization on a AV-8B Harrier strike aircraft is about 28% by weight, and composite structure utilization on a F/A-18 E/F Super Hornet strike fighter is about 20% by weight. Application of composite materials, such as carbon reinforced composite materials, is particularly valuable, because of performance improvements, component mass reduction, and relatively low manufacturing costs.

Many fiber-reinforced composite materials experience time-dependent micro-structural damage at loads far below their failure stress. Damage here refers to ply-level micro-structural changes such as matrix cracking and fiber—matrix debonding. Such micro-cracking can have significant softening effect in the off-axis fiber directions and may cause more serious forms of damage, such as transverse cracking, delamination, and finally fiber failure. As the load on fiber-reinforced composite materials increases, the effective stiffness may be reduced and an onset-of-damage may be observed which is caused by internal micro-cracks in the resin. The fatigue life capability of a composite material and, therefore, the capability to withstand repeated loading, are expected to be limited by the onset-of-damage, the micro-cracking. On the other hand, almost infinite fatigue life for repeated loading of carbon-reinforced composites is possible if the loading intensity is held below the initial formation of micro-cracks (onset-of-damage), as shown in FIG. 1. FIG. 1 (prior art) provides an x-y plot 10 showing the fatigue life of a carbon/epoxy composite material (trace 11) in comparison with metals and alloys (traces 12, 13, and 14). Consequently, it is very important to have a reliable method that can experimentally determine the presence and extent of micro-cracking.

To date, the best method to find micro-cracks is to apply a certain load of increasing load levels to many specimens (tensile coupon testing), to destructively cross section each of these specimens, prepare photomicrographs, and visually check for micro-cracks. Such method has been described, for example, by Scott T. Burr, David L. Sikarskie in "Damage Characterization of Woven Composites Under Static Tensile Stress", 1995 SEM Spring Conference and Exhibit, June 12–14, Grand Rapids, Mich., U.S.A. Despite the enormous time and test material expense, this method is not always successful since the micro-cracks may close when the load is released. Furthermore, the cross section may not have been taken at the exact location where micro-cracks exist.

Other prior art approaches to determine micro-cracking in composite materials include the acoustic emission method. During the application of a load to a composite material specimen, acoustic events emitted from a micro-crack can be recorded. Since the acoustic wavespeed changes with the fiber direction, the relative arrival time of an acoustic event emitted from a micro-crack may not be identical with the formation of the micro-crack. While the dynamic growth of a micro-crack can be monitored using the acoustic emission method, this method cannot reliably determine the initial formation of micro-cracks.

As can be seen, there is a need for a method to reliably determine the presence and extent of micro-cracking in carbon-reinforced composite materials. Furthermore, there is a need to experimentally determine the load that causes the initial formation of micro-cracks (onset-of-damage). Also, there is a need to obtain test results without destructive testing of many specimens.

There has, therefore, arisen a need to provide a method for determination of the formation and growth of micro-cracks in carbon-reinforced composite materials under load. There has still further arisen a need to provide an apparatus that enables the determination of the initial formation of macro-cracks in carbon-reinforced composite materials.

SUMMARY OF THE INVENTION

The present invention provides a test method for visual documentation of the formation and growth of micro-cracks in carbon-reinforced composite materials under tensile load. The present invention further provides a test unit that enables the determination of the initial formation of micro-cracks in carbon-reinforced composite materials under tensile load. The present invention still further enables determination of criteria that ensure almost unlimited fatigue life of a carbon-reinforced composite structure that may be used, but is not limited to, in the aerospace industry; for example, in modern strike aircraft and short take off-vertical landing tactical aircraft.

In one aspect of the present invention, a test method for visual documentation of micro-cracks during tensile coupon testing comprises the steps of: assembling a test unit including a tensile coupon testing machine, a stereomicroscope having a digital camera attached, a microscope light, and a camera strobe light; inserting a carbon-reinforced composite specimen having a prepared edge into the tensile coupon testing machine; illuminating the prepared edge of the specimen with the camera strobe light and the microscope light; applying a tensile load to the specimen using the tensile coupon testing machine; and capturing an image of the prepared edge of the specimen provided by the stereomicroscope with the digital camera.

In another aspect of the present invention, a method for assembling a test unit for visual documentation of micro-cracks during tensile coupon testing comprises the steps of: providing a test frame; rigidly fixing a lower test grip and an upper test grip to the test frame; rigidly fixing a stereomicroscope to the test frame; inserting the specimen made out of carbon-reinforced composite material into the lower test grip and the upper test grip; positioning a camera strobe light on the test frame; and illuminating an edge of the specimen with the camera strobe light and the microscope light. The lower test grip and the upper test grip are not free to rotate. The stereomicroscope includes a camera light and has a digital camera attached. The specimen has a prepared edge and a vertical orientation.

In still another aspect of the present invention, a method for specimen preparation for visual documentation of micro-cracks during tensile coupon testing comprises the steps of: manufacturing a specimen out of a carbon/cyanate ester having a woven quasi-isotropic layup; preparing an area of the edge of the specimen for photo microscopy; attaching a strain gage to the specimen; providing a lower test grip and an upper test grip; and inserting the specimen into the lower test grip and the upper test grip. The specimen extends longitudinally and has a thickness and at least one edge. The area extends longitudinally at least twice the thickness of the specimen. The specimen has a vertical orientation.

In a further aspect of the present invention, a method for determination of criteria ensuring almost unlimited fatigue life of carbon-reinforced composite structures comprises the steps of: providing a test unit including a lower test grip, an upper test grip, a stereomicroscope having a digital camera attached, a microscope light, and a camera strobe light; providing a specimen made out of a carbon-reinforced composite material and having a strain gage attached; preparing an edge of the specimen for photo microscopy; inserting the specimen into the lower test grip and the upper test grip; illuminating the prepared edge with the microscope light and the camera strobe light; applying a first tensile load to the specimen using the lower test grip and the upper test grip; capturing a first image provided by the stereomicroscope with the digital camera; measuring strain with the strain gage at the first tensile load; recording a first x-y plot showing tensile strength vs. strain; pairing the first image with the first x-y plot; applying a second tensile load to the specimen using the lower test grip and the upper test grip; capturing a second image provided by the stereomicroscope with the digital camera; measuring strain with the strain gage at the second tensile load; recording a second x-y plot showing tensile strength vs. strain; pairing the first image with the second x-y plot; observing first occurrence of micro-cracks in the first image; observing growth of the micro-cracks in the second image; determining tensile stress of the first occurrence of the micro-cracks; and providing the determined tensile stress to aerospace industry for avoiding fatigue failures of a carbon-reinforced composite structure manufactured out of said carbon reinforced composite material.

In still a further aspect of the present invention, a test method for visual documentation of the formation and growth of micro-cracks in carbon-reinforced composite materials during tensile coupon testing comprises the steps of: assembling a test unit including a lower test grip, an upper test grip, a stereomicroscope having a digital camera attached, a microscope light, and a camera strobe light; manufacturing a specimen out of a carbon/cyanate ester having a woven quasi-isotropic layup; preparing an area of the edge of the specimen for photo microscopy; attaching a strain gage to the specimen; inserting the specimen into the lower test grip and the upper test grip; applying a first tensile load of about 41% tensile strength to the specimen using the lower test grip and the upper test grip; providing a first image of the prepared edge of the specimen with the stereomicroscope; capturing the first image with the digital camera; measuring strain with the strain gage at the first tensile load; recording a first x-y plot showing tensile strength vs. strain; pairing the first image with the first x-y plot; applying a second tensile load of about 93% tensile strength to the specimen using the lower test grip and the upper test grip; providing a second image of the prepared edge of the specimen with the stereomicroscope; capturing the second image with the digital camera; measuring strain with the strain gage at the second tensile load; recording a second x-y plot showing tensile strength vs. strain; pairing the second image with the at least one additional x-y plot; observing first occurrence of micro-cracks in the first image; and observing growth of the micro-cracks in the second image. The specimen extends longitudinally and has a thickness and at least one edge. The area extends longitudinally at least twice the thickness of the specimen. The specimen has a vertical orientation.

In still another aspect of the present invention, a test unit comprises a test frame, a lower test grip and an upper test grip, both rigidly fixed to the test frame, a stereomicroscope including a microscope light rigidly fixed to the test frame, a digital camera attached to the stereomicroscope, and a camera strobe light attached to a ring stand and positioned on the test frame. The lower test grip and the upper test grip are rigidly fixed to the test frame.

These and other features, aspects and advantages of the present invention will become better understood with reference to the following drawings, description and claims.

DETAILED DESCRIPTION OF THE INVENTION

Figure 1:
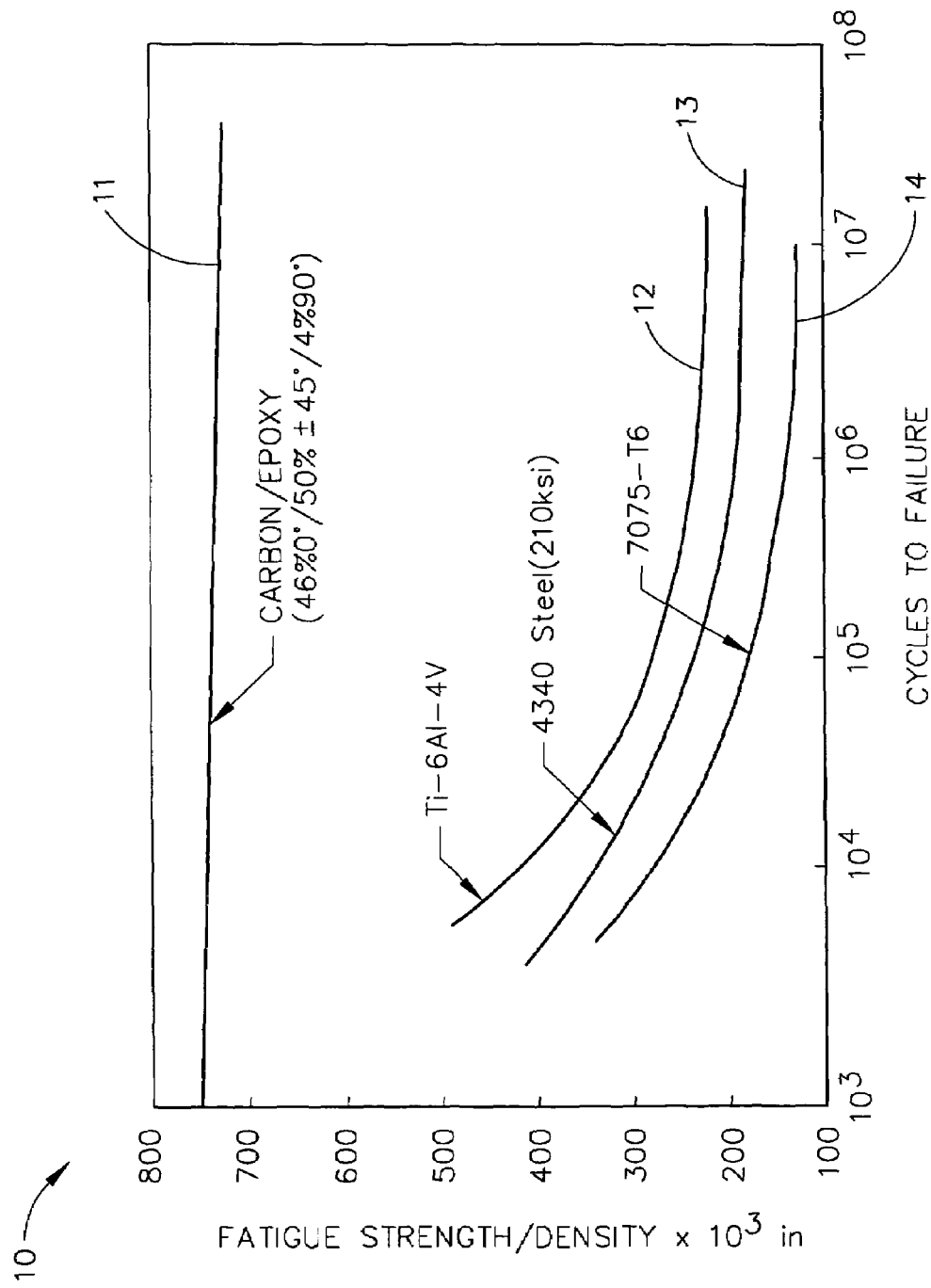
FIG. 1 is an x-y plot illustrating the fatigue life of different materials according to prior art.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, an embodiment of the present invention provides a test method for visual documentation of the formation and growth of micro-cracks in carbon-reinforced composite materials during tensile coupon testing. Contrary to the known prior art, only one specimen is needed to obtain information about formation and growth of micro-cracks in carbon-reinforced composite materials where currently destructive testing of many specimens is required. Furthermore, the test method according to one embodiment of the present invention will allow visually following the initial formation as well as the growth of existing micro-cracks under an increasing tensile load, which is not possible using the destructive prior art method. The test method as in one embodiment of the present invention may be used to determine the initial formation of micro-cracks in carbon-reinforced composite materials, such as carbon/cyanate ester and carbon (graphite)/epoxy. The test method as in one embodiment of the present invention further enables determination of criteria that ensure almost unlimited fatigue life of carbon-reinforced composite structures. Such carbon-reinforced structures may be used, but are not limited to, in the aerospace industry; for example, in modern strike aircraft, short take off-vertical landing tactical aircraft, and for spacecraft and launch vehicle structures.

In one embodiment, the present invention provides a photographic technique that allows viewing of a polished edge of a specimen over an area that is several times the specimen thickness while the specimen is under increasing tensile load. The photographic technique allows visually following the formation and growth of micro-cracks in carbon-reinforced composite materials under tensile load. The photographic technique further documents in-situ the initial formation of new micro-cracks, the growth of these micro-cracks, and the formation of new cracks as a function of a tensile load applied to the specimen as the load increases. Using prior art destructive test methods, visually following the formation and growth of micro-cracks is not possible, since the edge of a specimen may only be evaluated through destructively cross sectioning the specimen after a certain tensile load was applied to the specimen and then removed.

In one embodiment, the present invention provides a test method that enables photographic documentation of micro-cracks that occur in carbon-reinforced composite materials under tensile load during tensile coupon testing, whereas the prior art destructive test method may not be able to detect and, therefore, to document micro-cracks in carbon-reinforced composite materials. The prior art destructive test method may not be able to detect micro-cracks in carbon-reinforced composite materials since the micro-crack that occurs under load may close up when the load is removed and therefore, may not be visible in the cross section of the specimen after the load was removed. Furthermore, micro-cracks may not be visible using prior art destructive test methods, since the cross section of the specimen may not have been taken at the exact location where the micro-cracks exist.

In one embodiment, the present invention provides a digital camera attached to a stereomicroscope. The digital camera may include a strobe light that is used to light a prepared edge of the specimen under tensile load. The use of the strobe light removes the effect of vibration while the use of an incandescent light source included in the stereomicroscope adds color to the image. The lightening of the polished edge of the specimen under tensile load as in one embodiment of the present invention enables visibility of the micro-cracks in the specimen under tensile load. The micro-cracks will not be visible unless the edge of the specimen is properly prepared and lighted. Contrary to the test method as in one embodiment of the present invention, the prior art destructive test method only utilizes a stereomicroscope to examine the prepared cross section of the specimen after the tensile load was removed.

Figure 2:
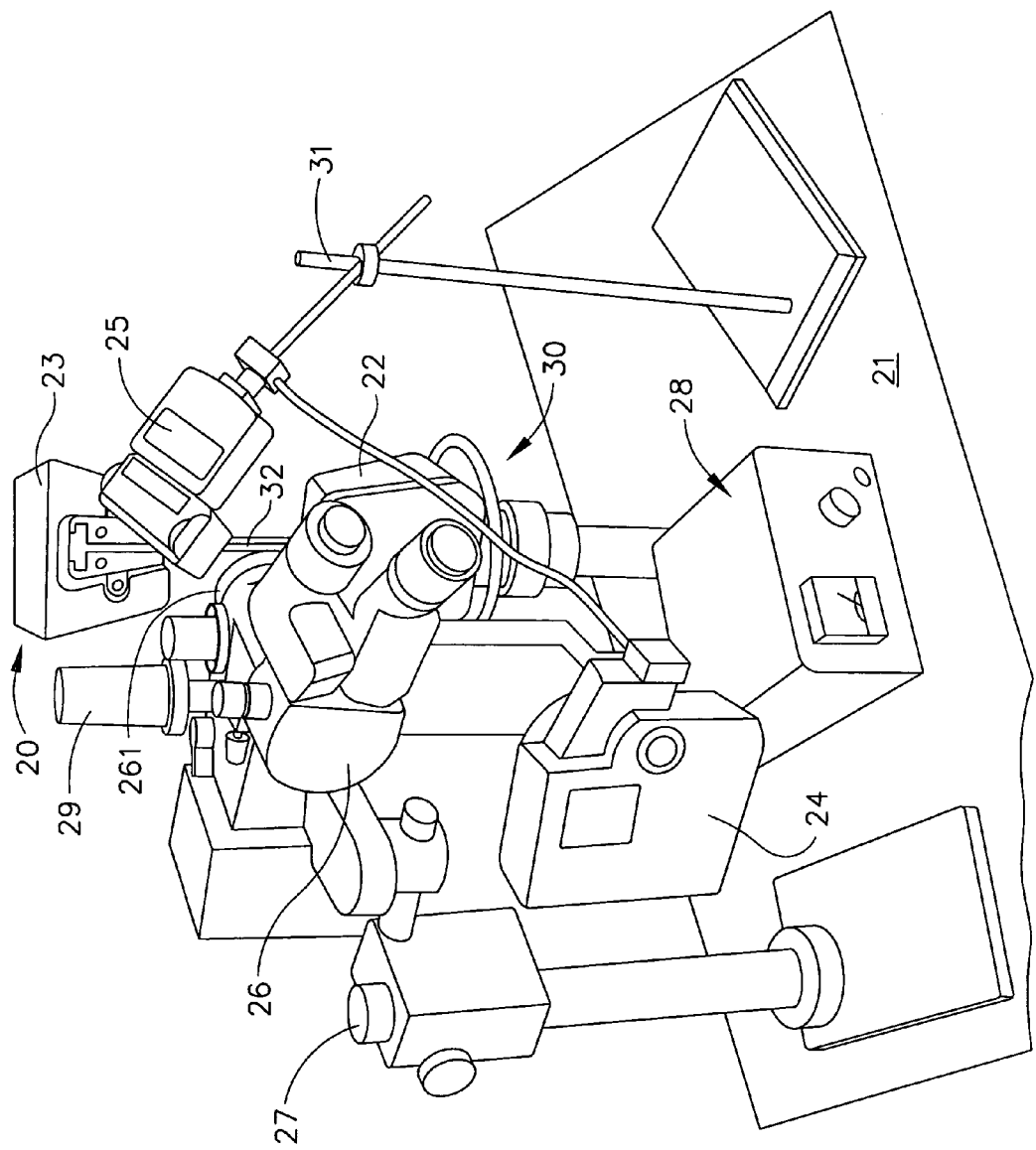
FIG. 2 is a perspective front view of a test unit according to one embodiment of the present invention.

Referring now to FIG. 2, a test unit 20 is illustrated according to one embodiment of the present invention. The test unit 20 may include a test frame 21, a lower test grip 22, an upper test grip 23, a digital camera 24, a camera strobe light 25, and a stereomicroscope 26. The lower test grip 22 and the upper test grip 23 may be part of a tensile coupon testing machine 30. The lower test grip 22, the upper test grip 23, and the stereomicroscope 26 may be rigidly fixed to the test frame 21. The lower test grip 22 and the upper test grip 23 may be rigidly fixed to the test frame 21 such that they may not be free to rotate. Rigidly attaching the lower test grip 22 and the upper test grip 23 facilitates the alignment of the stereomicroscope 26 and the camera strobe light 25 for multiple specimens testing. The lower test grip 22 and the upper test grip 23 may be hydraulic test grips. The lower test grip 22 and the upper test grip 23 may hold a specimen 32 in vertical direction. The lower test grip 22 and the upper test grip 23 may be used to apply a static tensile load to the specimen 32. The test unit 20 may further include a microscope support stage 27 that may be used to rigidly attach the stereomicroscope 26 to the test frame 21. The microscope support stage 27 may also provide coarse and fine adjustment of the stereomicroscope 26. The stereomicroscope 26 may include a focus adjustment knob 29 and a microscope light 261. A microscope light power source 28 may supply power to the microscope light 261 of the stereomicroscope 26. The microscope light 261 of the stereomicroscope 26 may be an incandescent light source. The digital camera 24 may be attached to the stereomicroscope 26, as shown in FIG. 1, to capture images provided by the microscope 26.

Figure 3:
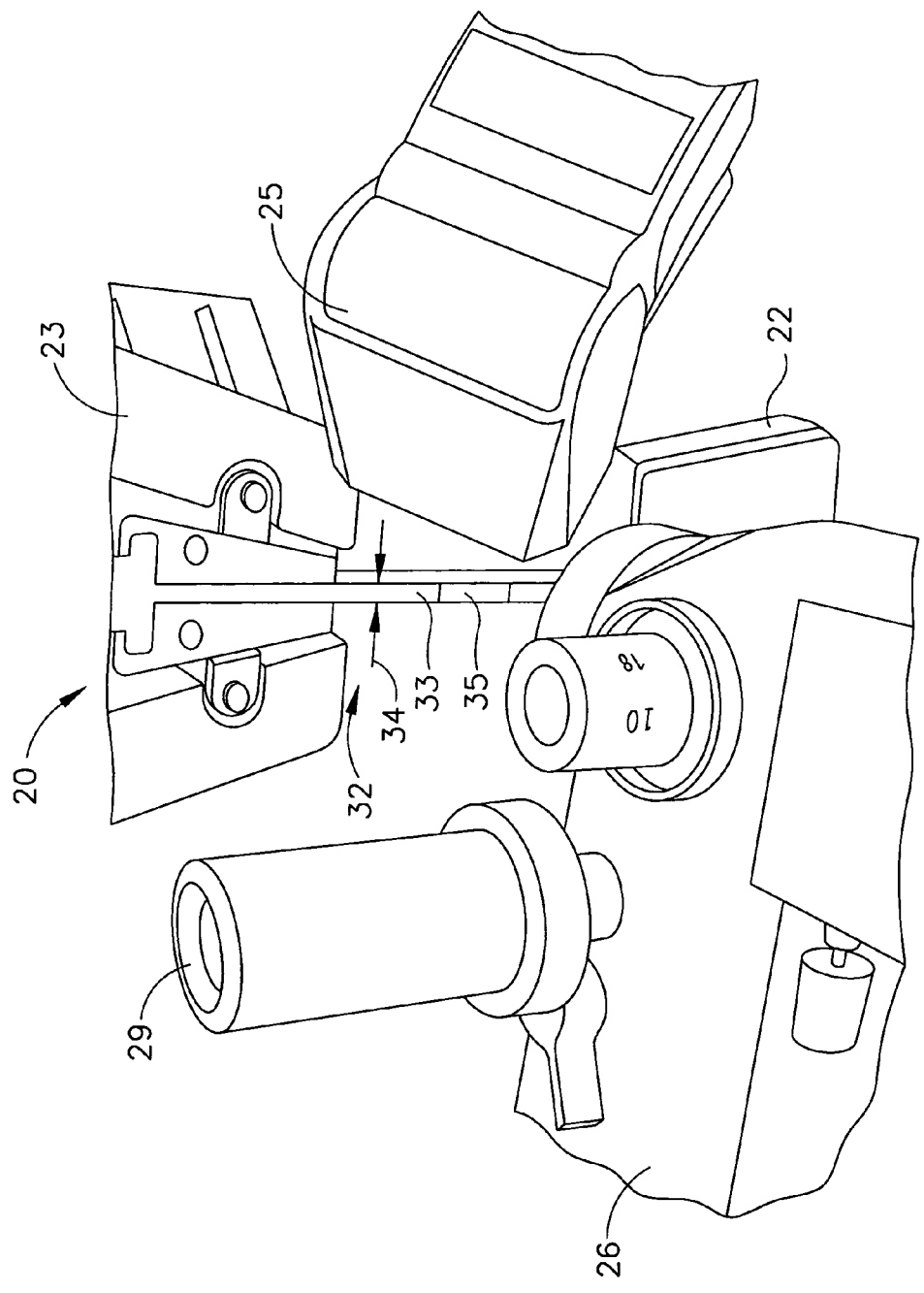
FIG. 3 is a perspective front view of a detail of the test unit illustrated in FIG. 2 according to one embodiment of the present invention.
Figure 3A:
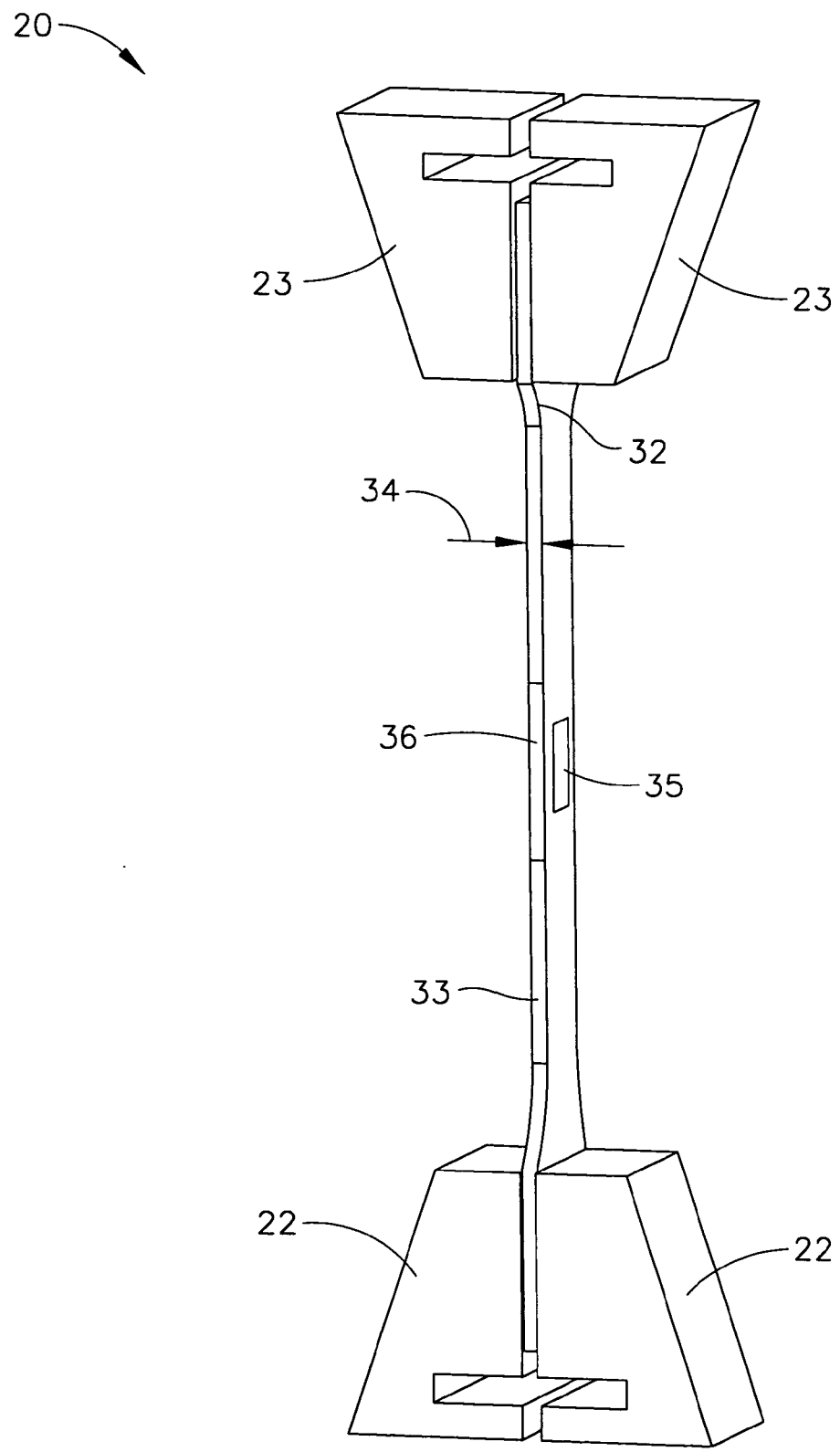
FIG. 3a is a perspective front view of another detail of the test unit illustrated in FIG. 2 according to one embodiment of the present invention.

Referring now to FIGS. 3 and 3a, details of the test unit 20 (illustrated in FIG. 2) are illustrated according to one embodiment of the present invention. A specimen 32 may be inserted in the lower test grip 22 and in the upper test grip 23, such that the specimen 32 has a vertical orientation. The specimen 32 may be made out of a carbon-reinforced composite material, such as carbon (graphite)/epoxy and carbon/cyanate ester. The specimen 32 may extend longitudinally and may be a dog bone shaped tensile coupon, as illustrated in FIGS. 3 and 3a, or a straight-sided rectangular tensile coupon not illustrated). The dog-bone shape of the specimen 32 as shown in FIG. 3a is the preferred shape since this shape forces the failure of the specimen 32 under increasing tensile load to occur in the center of the specimen 32. The specimen 32 may further have an edge 33. An area 36 of the edge 33 may be prepared for photo microscopy. The prepared area 36 of the edge 33 may extend longitudinally at least twice the thickness 34 of the specimen 32. The edge 33 of the specimen 32 may be prepared by wet sanding followed by polishing. For the wet sanding, silicone carbide sanding papers with different grits may be used. The polishing may include two steps using wafer soluble h-micron diamond paste and a hard surfaced metallurgical polishing cloth, for example, Texmet, a Buehler Metallurgical Supplies product. A new polishing cloth may be used for each of the polishing steps. The polished area 36 may be cleaned between the two polishing steps. Furthermore, a strain gage 35 may be attached to the specimen 32. The strain gage 35 may be used to measure the tensile strain of the specimen 32 once a static tensile load is applied to the specimen 32 using the lower test grip 22 and the upper test grip 23. Strain is defined as the amount of deformation per unit length of a specimen 32 when a load is applied. Strain may be calculated by dividing the total deformation of the original length by the original length or may be measured using a strain gage 35. The strain gage 35 may convert the mechanical motion into an electric signal. A change in, for example, capacitance, inductance, or resistance is proportional to the strain experienced by the strain gage 35.

As illustrated in FIGS. 2 and 3, the camera strobe light 25 may be attached to a ring stand 31 and positioned such that the strobe light 25 is illuminating the prepared edge 33 of the specimen 32 while being held in the test grips 22 and 23. The stereomicroscope 26 may be also positioned such that the microscope light 261 is projected through the lens onto the prepared area 36 of the edge 33 of the specimen 32 while being held in the test grips 22 and 23. Images provided by the stereomicroscope 26 may be captured with the digital camera 24 attached to the microscope 26. The images captured by the digital camera 24 may be saved on a smart media card for later processing. The processing of the images may be done using editing software, for example, Microsoft Photo Draw.

Figure 4B:
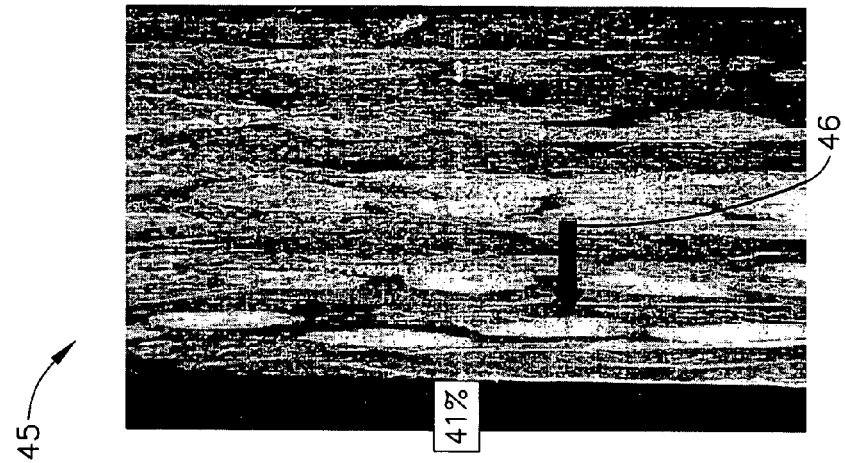
FIG. 4b is an image of a carbon/cyanate ester specimen taken at 41% tensile strength according to one embodiment of the present invention.
Figure 5B:
FIG. 5b is an image of a carbon/cyanate ester specimen taken at 93% tensile strength according to one embodiment of the present invention.
Figures 6A, 6B:
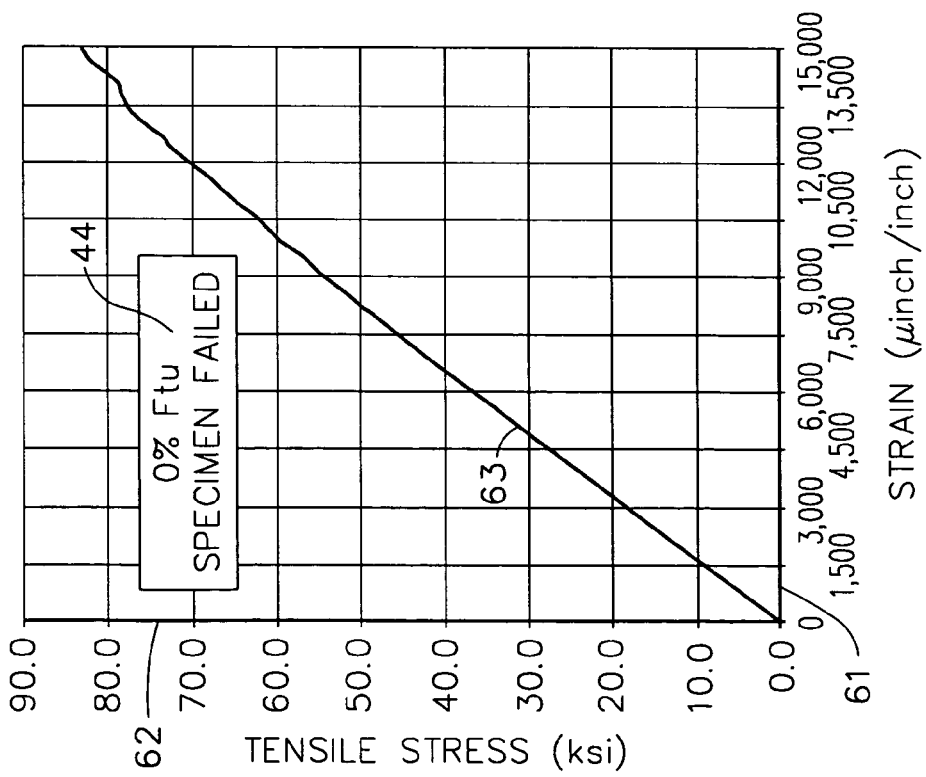
FIG. 6a is an x-y plot showing tensile stress vs. strain of a carbon/cyanate ester specimen at 0% tensile strength (specimen failed) according to one embodiment of the present invention.
FIG. 6b is an image taken of a carbon/cyanate ester specimen taken at 0% tensile strength after specimen failure according to one embodiment of the present invention.

Once the test unit 20 has been set up as described and the specimen 32 has been inserted in the lower test grip 22 and the upper test grip 23, a static tensile load may be applied to the specimen 32 using the tensile coupon testing machine 30. The tensile load may start at 0% tensile strength (no load) and may be increased steadily until failure of specimen 32 occurs. The tensile strength (Ftu) may be determined as the force per unit area (stress) that a material loaded in axial tension can carry before fracture occurs. The digital camera 24 may capture images of the prepared edge 33 of the specimen 32 at certain percentages of the tensile strength, for example, at 10% increments of the expected failing stress. The failing stress may be determined upfront in an independent tensile coupon test using another specimen 32. FIGS. 4b, 5b, and 6b show captured images of the prepared edge 33 of the specimen 32 at 41%, at 93%, and at 0% (specimen 32 failed) of the tensile strength, respectively. The strain gage 35 may measure the strain of the specimen 32 under tensile load and a tensile stress vs. tensile strain plot, for example, plot 40, plot 50, and plot 60, may be recorded during application of a continuously tensile load to the specimen 32. The images, for example, images 45, 55, and 65 captured with the digital camera 24 may be named sequentially such that the images may be paired later with the tensile stress vs. tensile strain plot according to the applied tensile load.

Figure 4A:
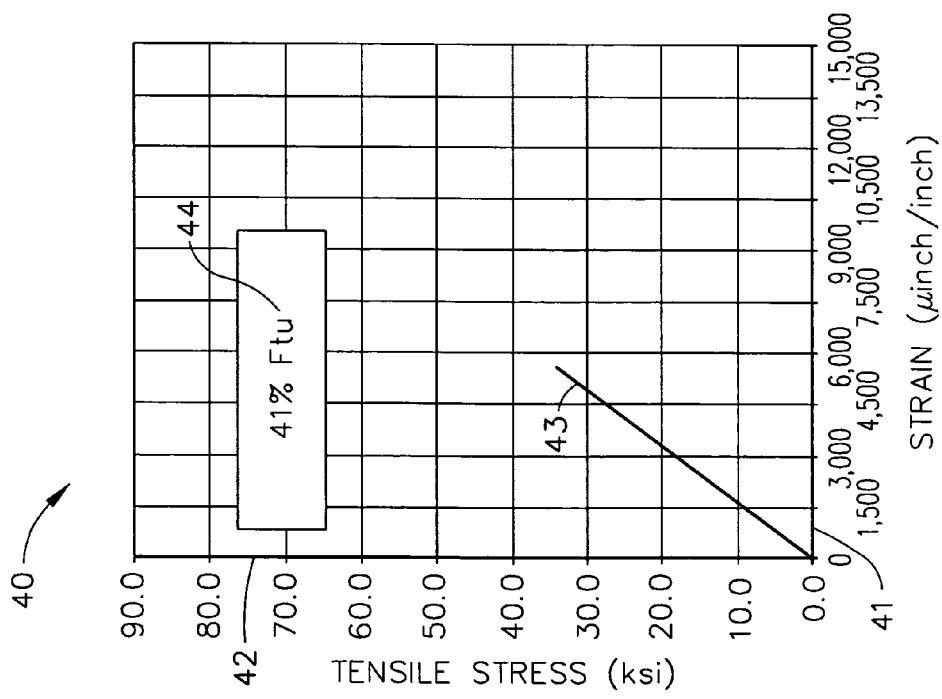
FIG. 4a is an x-y plot showing tensile stress vs. strain of a carbon/cyanate ester specimen at 41% tensile strength according to one embodiment of the present invention.

Referring now to FIGS. 4a and 4b, an x-y plot 40 showing tensile stress vs. strain and an image 45 taken of a carbon/cyanate ester specimen 32 at a tensile load 44 of 41% of the tensile strength are illustrated, respectively, according to one embodiment of the present invention. The plot 40 may include an x-axis 41 showing the strain measured in units of pinch/inch and a y-axis 42 showing the tensile stress measured in units of kips per square inch (ksi). The plot 40 may further include a trace 43 that shows the tensile stress and the strain of a specimen 32 under a load 44 of 41% tensile strength at room temperature. The plot 40 was recorded for a carbon/cyanate ester specimen 32 having a woven quasi-isotropic layup. The specimen 32 may have a width of about 0.50 inches and thickness 34 of about 0.179 inches. The image 45 was taken of the prepared edge 33 of the carbon/cyanate ester specimen 32 having a woven quasi-isotropic layup while a load 44 of 41% tensile strength was applied to the specimen 32. A first micro-crack 46 may be observed at this tensile load 44 at room temperature.

Figure 5A:
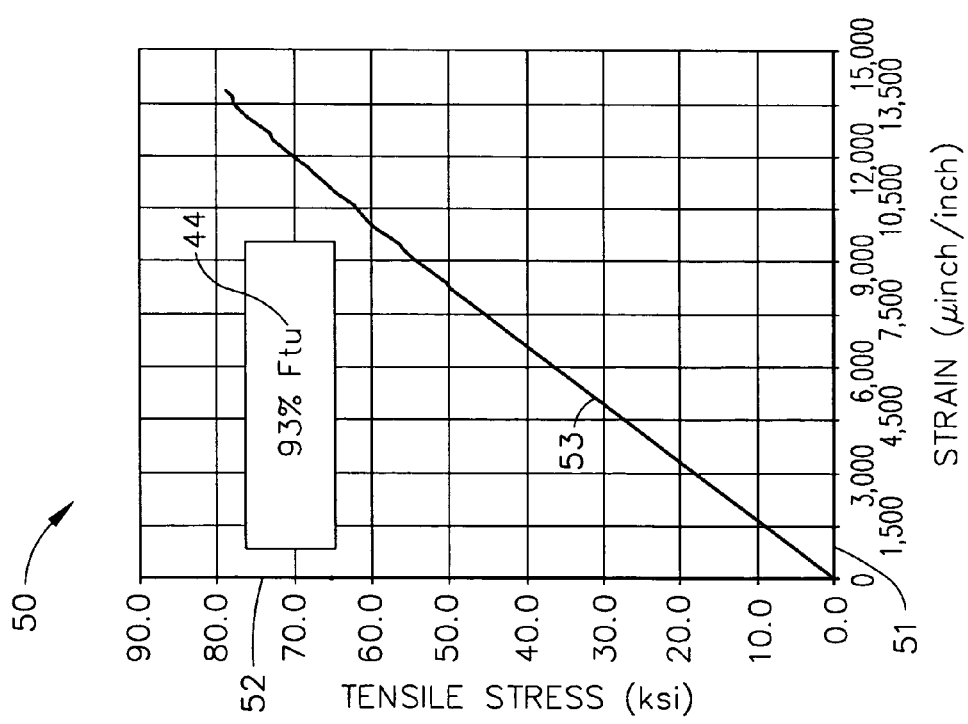
FIG. 5a is an x-y plot showing tensile stress vs. strain of a carbon/cyanate ester specimen at 93% tensile strength according to one embodiment of the present invention.

Referring now to FIGS. 5a and 5b, an x-y plot 50 showing tensile stress vs. strain and an image 55 taken of a carbon/cyanate ester specimen 32 at a tensile load 44 of 93% of the tensile strength are illustrated, respectively, according to one embodiment of the present invention. The plot 50 may include an x-axis 51 showing the strain measured in units of pinch/inch and a y-axis 52 showing the tensile stress measured in units of kips per square inch (ksi). The plot 50 may further include a trace 53 that shows the tensile stress and the strain of a specimen 32 under a load 44 of 93% tensile strength at room temperature. The plot 50 was recorded for a carbon/cyanate ester specimen 32 having a woven quasi-isotropic layup. The specimen 32 may have a width of about 0.50 inches and thickness 34 of about 0.179 inches. The image 55 was taken of the prepared edge 33 of the carbon/cyanate ester specimen 32 having a woven quasi-isotropic layup while a load 44 of 93% tensile strength was applied to the specimen 32. As can be seen in FIG. 5b, the micro-crack 46 first observed at a tensile load 44 of 41% tensile strength may have grown and other micro-cracks 56 may have formed and grown under the increasing tensile load 44.

Referring now to FIGS. 6a and 6b, an x-y plot 60 showing tensile stress vs. strain and an image 65 taken of a carbon/cyanate ester specimen 32 at a tensile load 44 of 0% of the tensile strength after failure of specimen 32 are illustrated, respectively, according to one embodiment of the present invention. The plot 60 may include an x-axis 61 showing the strain measured in units of pinch/inch and a y-axis 62 showing the tensile stress measured in units of kips per square inch (ksi). The plot 60 may further include a trace 63 that shows the tensile stress and the strain of a specimen 32 under a load 44 of 0% tensile strength after the specimen 32 failed. The tensile load 44 was applied to the specimen at room temperature. The plot 60 was recorded for a carbon/cyanate ester specimen 32 having a woven quasi-isotropic layup. The specimen 32 may have a width of about 0.50 inches and thickness 34 of about 0.179 inches. The image 65 was taken of the prepared edge 33 of the carbon/cyanate ester specimen 32 having a woven quasi-isotropic layup while a tensile load 44 leading to the failure of the specimen 32 was applied to the specimen 32. As can be seen in FIG. 6b, after the tensile load 44 is released (0% of tensile strength), due to the failure of the specimen 32 the micro-cracks visible in FIG. 5b may close and may not be detectable in the image 65.

Figure 7:
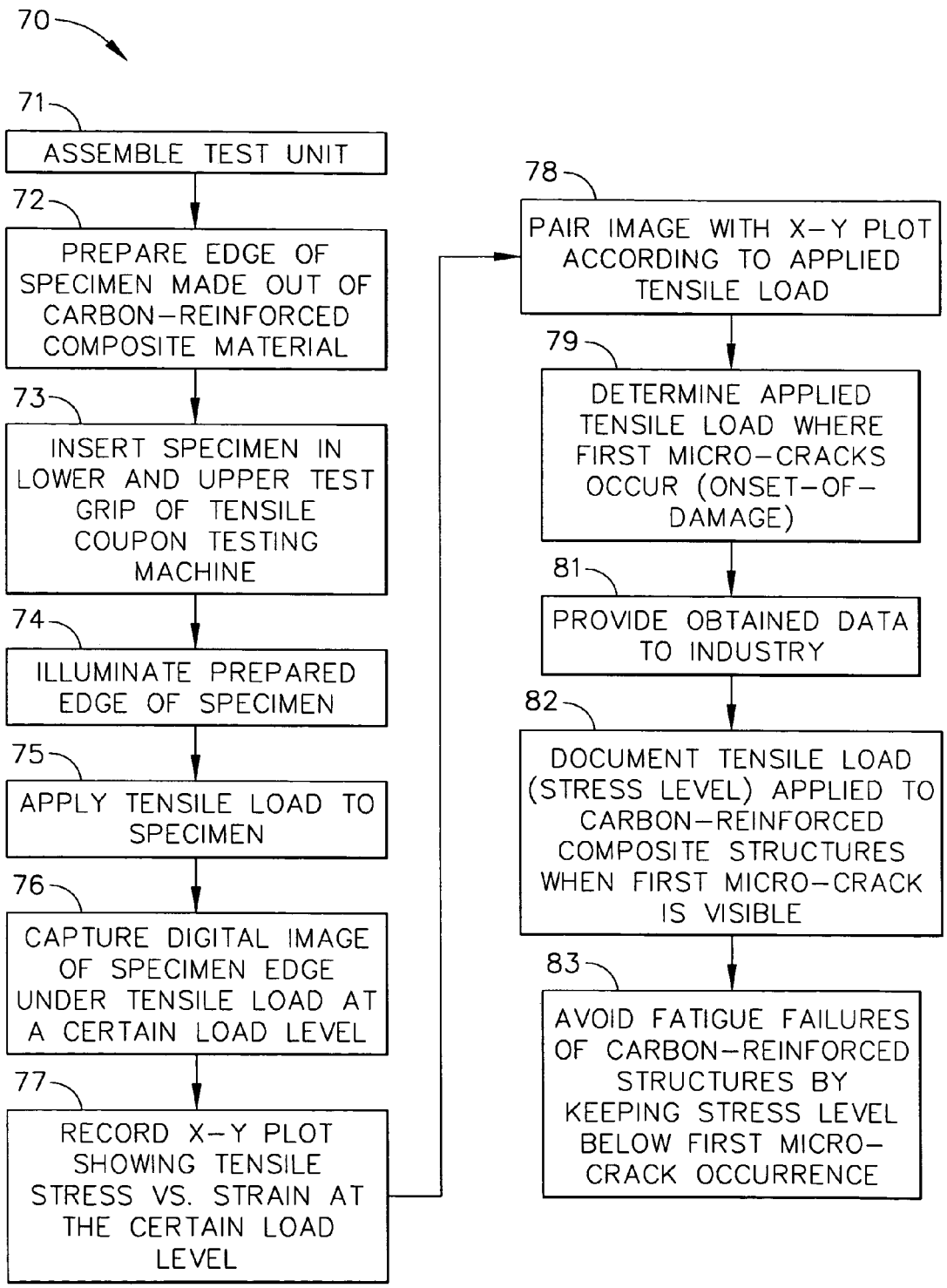
FIG. 7 is a flow chart of a test method for visual documentation of the formation and growth of micro-cracks in carbon-reinforced composite materials during tensile coupon testing according to another embodiment of the present invention.

Referring now to FIG. 7, a block diagram of a method 70 for visual documentation of the formation and growth of micro-cracks 46 and 56 in carbon-reinforced composite materials during tensile coupon testing is illustrated according to another embodiment of the present invention. The test method 70 may include the steps of: assembling the test unit 20 as shown in FIGS. 2 and 3 (step 71); inserting a specimen 32 in a tensile coupon testing machine 30 (step 73); illuminating the specimen 32 (step 74); applying a tensile load 44 to the specimen 32 (step 75); visually documenting the formation and growth of micro-cracks, for example, micro-cracks 46 and 56 shown in FIGS. 4b and 5b, respectively (steps 76, 77, and 78); and interpreting of obtained test data (step 79). The step 75 of the test method 70 may also include the steps of: determining failing stress of the specimen 32 and increasing the tensile load 44 applied to the specimen 32 at 10% increments of the failing stress. The step 76 of the test method 70 may further include the step of capturing images (such as images 45, 55, and 65) provided by the stereomicroscope 26 with the digital camera 24 at 10% increments of the expected failing stress. The test method 70 may further include the steps of: manufacturing a specimen 32, for example, a dog-bone shaped tensile coupon (as shown in FIGS. 2 and 3), out of a carbon-reinforced composite material; and preparing an edge 33 of the specimen 32 (step 72). The test method 70 may still further include the steps of: providing the obtained data to the industry (step 81); and documenting the tensile load 44 and, therefore, the stress level, applied to carbon-reinforced composite structures when first micro-crack 46 is visible, as shown in FIGS. 4a and 4b (step 82). By following step 81 and 82 of the test method 70 and by keeping the stress level of a carbon-reinforced composite structure below the first micro-crack occurrence, fatigue failures of carbon-reinforced structures may be avoided (step 83). Step 72 may include manufacturing the specimen 32 out of carbon/cyanate ester having a woven quasi-isotropic layup and wet sand and polishing the edge 33 of the specimen 32. Step 72 may still further include attaching a strain gage 35 to the specimen 32, as shown in FIGS. 2 and 3. Step 73 may include inserting the specimen 32 in the lower test grip 22 and the upper test grip 23 of a tensile coupon testing machine 30, as shown in FIGS. 2 and 3. Assembling the test unit 20 in step 71 may include the steps of: attaching the lower test grip 22, the upper test grip 23, and the stereomicroscope 26 having a digital camera 24 attached, rigidly to the test frame 21. The test method 70 may further include illuminating the prepared edge 33 of the specimen 32 using the camera strobe light 25 and the microscope light 261 of the stereomicroscope 26 in step 74. By illuminating a prepared edge 33 the carbon-reinforced composite specimen 32 under tensile load 44 with the camera strobe light 25 in addition to the microscope light 261 of the stereomicroscope 26, as in step 74, the effect of vibration of the specimen 32 during application of the tensile load 44 may be removed. Consequently, the formation and growth of micro-cracks, for example, micro-crack 46 (FIG. 4b) and micro-crack 56 (FIG. 5b) may be viewed through the stereomicroscope 26 and may be documented using the attached digital camera 24. The photographic technique developed may allow viewing of a prepared edge 33 of a carbon-reinforced specimen 32 and may allow in-situ documentation of the initial formation and growth of micro-cracks as a function of the tensile load 44 applied to the specimen 32 while the tensile load 44 increases (as in FIGS. 4a to 6b).

It should be understood, of course, that the foregoing relates to exemplary embodiments of the invention and that modifications may be made without departing from the spirit and scope of the invention as set forth in the following claims.

We claim:

1. A test method for visual documentation of micro-cracks during tensile coupon testing, comprising the steps of:

assembling a test unit including a tensile coupon testing machine, a stereomicroscope having a digital camera attached, a microscope light, and a camera strobe light;

wet sanding an area of an edge of a carbon-reinforced composite specimen using silicon carbide sanding papers having different grits;

polishing said area using wafer soluble h-micron diamond paste and a first hard surfaced metallurgical polishing cloth;

cleaning said area; and polishing said area using wafer soluble h-micron diamond paste and a second hard surfaced metallurgical polishing cloth;

inserting said carbon-reinforced composite specimen into said tensile coupon testing machine;

illuminating said prepared edge of said specimen with said camera strobe light and said microscope light;

applying a tensile load to said specimen using said tensile coupon testing machine; and capturing an image of said area of said specimen provided by said stereomicroscope with said digital camera.

2. The test method for visual documentation of micro-cracks during tensile coupon testing of claim 1, further comprising the step of manufacturing said specimen out of a carbon/cyanate ester having a quasi-isotropic layup.

3. The test method for visual documentation of micro-cracks during tensile coupon testing of claim 1, further comprising the step of manufacturing said specimen as a dog bone shaped tensile coupon.

4. The test method for visual documentation of micro-cracks during tensile coupon testing of claim 1, further comprising the steps of providing said specimen having a thickness and preparing said edge of said specimen, wherein said edge extends longitudinally several times the thickness of said specimen.

5. The test method for visual documentation of micro-cracks during tensile coupon testing of claim 1, further comprising the step of attaching a strain gage to said specimen.

6. The test method for visual documentation of micro-cracks during tensile coupon testing of claim 1, further comprising the step of increasing said tensile load starting at about 0% tensile strength until failure of said specimen occurs.

7. The test method for visual documentation of micro-cracks during tensile coupon testing of claim 1, further comprising the step of recording a x-y plot showing tensile stress vs. strain for said tensile load.

8. The test method for visual documentation of micro-cracks during tensile coupon testing of claim 1, further comprising the step of determining said tensile load that causes initial forming of micro-cracks within said specimen.

9. The test method for visual documentation of micro-cracks during tensile coupon testing of claim 1, further comprising the steps of manufacturing a carbon-reinforced composite structure; experimentally determining tensile load for said carbon-reinforced material that causes initial forming of micro-cracks; and keeping load applied to said structure under said experimentally determined tensile load.

10. A method for assembling a test unit for visual documentation of micro-cracks during tensile coupon testing, comprising the steps of:

providing a test frame;

rigidly fixing a lower test grip and an upper test grip to said test frame, wherein said lower test grip and said upper test grip are not free to rotate;

rigidly fixing a stereomicroscope to said test frame, wherein said stereomicroscope includes a camera light and has a digital camera attached;

wet sanding an area of an edge of a carbon-reinforced composite specimen using silicon carbide sanding papers having different grits;

polishing said area using wafer soluble h-micron diamond paste and a first hard surfaced metallurgical polishing cloth;

cleaning said area; and polishing said area using wafer soluble h-micron diamond paste and a second hard surfaced metallurgical polishing cloth;

inserting said carbon-reinforced specimen into said lower test grip and said upper test grip, wherein said specimen has a vertical orientation;

positioning a camera strobe light on said test frame; and illuminating an edge of said specimen with said camera strobe light and said microscope light.

11. The method for assembling a test unit for visual documentation of micro-cracks during tensile coupon testing of claim 10, further comprising the steps of:

applying a static tensile load to said specimen using said lower test grip and said upper test grip;

providing an image of said prepared edge of said specimen with said stereomicroscope; and capturing said image with said digital camera.

12. The method for assembling a test unit for visual documentation of micro-cracks during tensile coupon testing of claim 10, further comprising the step of attaching said camera strobe light to a ring stand.

13. The method for assembling a test unit for visual documentation of micro-cracks during tensile coupon testing of claim 10, further comprising the step of using a microscope support stage for attaching said stereomicroscope to said test frame.

14. The method for assembling a test unit for visual documentation of micro-cracks during tensile coupon testing of claim 13, further comprising the steps of:

coarse adjusting said stereomicroscope with said microscope support stage; and fine adjusting said stereomicroscope with said microscope support stage.

15. The method for assembling a test unit for visual documentation of micro-cracks during tensile coupon testing of claim 13, further comprising the step of selecting said carbon-reinforced composite material from the group of carbon (graphite)/epoxy and carbon/cyanate ester.

16. The method for assembling a test unit for visual documentation of micro-cracks during tensile coupon testing of claim 13, further comprising the step of saving said image on a smart media card for later processing.

17. A method for specimen preparation for visual documentation of micro-cracks during tensile coupon testing, comprising the steps of:

manufacturing a specimen out of a carbon/cyanate ester having a woven quasi-isotropic layup, wherein said specimen extends longitudinally and has a thickness and at least one edge;

preparing an area of said edge of said specimen for photo microscopy, wherein said area extends longitudinally at least twice the thickness of said specimen and wherein preparing said edge comprises wet sanding an area of an edge of said specimen using silicon carbide sanding papers having different grits, polishing said area using wafer soluble h-micron diamond paste and a first hard surfaced metallurgical polishing cloth, cleaning said area, and polishing said area using wafer soluble h-micron diamond paste and a second hard surfaced metallurgical polishing cloth;

attaching a strain gage to said specimen;

providing a lower test grip and an upper test grip; and inserting said specimen into said lower test grip and said upper test grip, wherein said specimen has a vertical orientation.

18. The method for specimen preparation for visual documentation of micro-cracks during tensile coupon testing of claim 17, further comprising the step of manufacturing said specimen as a dog bone shaped tensile coupon.

19. The method for specimen preparation for visual documentation of micro-cracks during tensile coupon testing of claim 17, further comprising the step of manufacturing said specimen as a straight-sided rectangular tensile coupon.

20. A method for determination of criteria ensuring almost unlimited fatigue life of carbon-reinforced composite structures, comprising the steps of:

providing a test unit including a lower test grip, an upper test grip, a stereomicroscope having a digital camera attached, a microscope light, and a camera strobe light;

providing a specimen made out of a carbon-reinforced composite material and having a strain gage attached;

preparing an edge of said specimen for photo microscopy wherein preparing said edge comprises wet sanding an area of the edge using silicon carbide sanding papers having different grits, polishing said area using wafer soluble h-micron diamond paste and a first hard surfaced metallurgical polishing cloth, cleaning said area, and polishing said area using wafer soluble h-micron diamond paste and a second hard surfaced metallurgical polishing cloth;

inserting said specimen into said lower test grip and said upper test grip;

illuminating said prepared edge with said microscope light and said camera strobe light;

applying a first tensile load to said specimen using said lower test grip and said upper test grip;

capturing a first image provided by said stereomicroscope with said digital camera;

measuring strain with said strain gage at said first tensile load;

recording a first x-y plot showing tensile strength vs. strain;

pairing said first image with said first x-y plot;

applying a second tensile load to said specimen using said lower test grip and said upper test grip;

capturing a second image provided by said stereomicroscope with said digital camera;

measuring strain with said strain gage at said second tensile load;

recording a second x-y plot showing tensile strength vs. strain;

pairing said first image with said second x-y plot;

observing first occurrence of micro-cracks in said first image;

observing growth of said micro-cracks in said second image;

determining tensile stress of said first occurrence of said micro-cracks; and providing said determined first micro-crack tensile stress to aerospace industry for avoiding fatigue failures of a carbon-reinforced composite structure manufactured out of said carbon reinforced composite material.

21. The method for determination of criteria ensuring almost unlimited fatigue life of carbon-reinforced composite structures of claim 20, further comprising the steps of:
applying at least one additional tensile load to said specimen using said lower test grip and said upper test grip;
capturing at least one additional image provided by said stereomicroscope with said digital camera;
measuring strain with said strain gage at said at least one additional tensile load;
recording a first x-y plot showing tensile strength vs. strain;
pairing said at least one additional image with said first x-y plot; and
pairing said at least one additional image with said first x-y plot.

22. The method for determination of criteria ensuring almost unlimited fatigue life of carbon-reinforced composite structures of claim 20, further comprising the steps of:
determining failing stress of said specimen;
increasing the tensile load applied to said specimen at 10% increments of said failing stress; and
capturing said first image, said second image, and said additional image provided by said stereomicroscope with said digital camera at said 10% increments of said failing stress.

23. The method for determination of criteria ensuring almost unlimited fatigue life of carbon-reinforced composite structures of claim 20, further comprising the step of using said carbon-reinforced composite structure in modern strike aircraft.

24. The method for determination of criteria ensuring almost unlimited fatigue life of carbon-reinforced composite structures of claim 20, further comprising the step of using said carbon-reinforced composite structure in short take off-vertical landing tactical aircraft.

25. A test method for visual documentation of the formation and growth of micro-cracks in carbon-reinforced composite materials during tensile coupon testing, comprising the steps of:
assembling a test unit including a lower test grip, an upper test grip, a stereomicroscope having a digital camera attached, a microscope light, and a camera strobe light;
manufacturing a specimen out of a carbon/cyanate ester having a woven quasi-isotropic layup, wherein said specimen extends longitudinally and has a thickness and at least one edge;
preparing an area of said edge of said specimen for photo microscopy,
wherein preparing an area comprises wet sanding said area using silicon carbide sanding papers having different grits, polishing said area using wafer soluble h-micron diamond paste and a first hard surfaced metallurgical polishing cloth, cleaning said area, and polishing said area using wafer soluble h-micron diamond paste and a second hard surfaced metallurgical polishing cloth, and
wherein said area extends longitudinally at least twice the thickness of said specimen;
attaching a strain gage to said specimen;
inserting said specimen into said lower test grip and said upper test grip, wherein said specimen has a vertical orientation;
applying a first tensile load of about 41% tensile strength to said specimen using said lower test grip and said upper test grip;
providing a first image of said prepared edge of said specimen with said stereomicroscope;
capturing said first image with said digital camera;
measuring strain with said strain gage at said first tensile load;
recording a first x-y plot showing tensile strength vs. strain;
pairing said first image with said first x-y plot;
applying a second tensile load of about 93% tensile strength to said specimen using said lower test grip and said upper test grip;
providing a second image of said prepared edge of said specimen with said stereomicroscope;
capturing said second image with said digital camera;
measuring strain with said strain gage at said second tensile load;
recording a second x-y plot showing tensile strength vs. strain;
pairing said second image with said at least one additional x-y plot;
observing first occurrence of micro-cracks in said first image; and
observing growth of said micro-cracks in said second image.

26. The test method for visual documentation of the formation and growth of micro-cracks in carbon-reinforced composite materials during tensile coupon testing of claim 25, further comprising the steps of:
determining tensile stress of said first occurrence of said micro-cracks;
providing said determined tensile stress to industry;
keeping load applied to a structure manufactured out of said carbon-reinforced composite material below said determined tensile stress; and
avoiding fatigue failures of said carbon-reinforced composite structure.

27. The test method for visual documentation of the formation and growth of micro-cracks in carbon-reinforced composite materials during tensile coupon testing of claim 25, further comprising the step of:
manufacturing said specimen as a dog bone shaped tensile coupon having a width of about 0.50 inches and thickness of about 0.179 inches.

28. A test unit, comprising:
a test frame;
a lower test grip and an upper test grip, both rigidly fixed to said test frame;
a carbon-reinforced composite specimen having a prepared edge;
a stereomicroscope including a microscope light rigidly fixed to said test frame;
a digital camera attached to said stereomicroscope; and
a camera strobe light attached to a ring stand and positioned on said test frame
wherein said prepared edge is prepared by wet sanding an area of said edge using silicon carbide sanding papers having different grits, polishing said area using wafer soluble h-micron diamond paste and a first hard surfaced metallurgical polishing cloth, cleaning said area, and polishing said area using wafer soluble h-micron diamond paste and a second hard surfaced metallurgical polishing cloth.

29. The test unit of claim 28, further comprising a microscope power light source providing power to said microscope light.

30. The test unit of claim 28, further comprising a microscope support stage used to rigidly attach said stereomicroscope to said test frame, wherein said microscope support stage provides coarse and fine adjustment of said stereomicroscope.

31. The test unit of claim 28, wherein said specimen is inserted vertically in said lower test grip and said upper test grip, and wherein a tensile load is applied to said specimen with said lower test grip and said upper test grip.

32. The test unit of claim 31, where in said specimen is illuminated with said camera strobe light and said microscope light.

33. The test unit of claim 28, wherein said lower test grip and said upper test grip comprise hydraulic test grips.

* * * * *